United States Patent
Tang et al.

(10) Patent No.: US 7,573,973 B2
(45) Date of Patent: Aug. 11, 2009

(54) METHODS AND SYSTEMS TO FACILITATE REDUCING CONE BEAM ARTIFACTS IN IMAGES

(75) Inventors: Xiangyang Tang, Waukesha, WI (US); Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 377 days.

(21) Appl. No.: 11/130,769

(22) Filed: May 17, 2005

(65) Prior Publication Data
US 2006/0262893 A1 Nov. 23, 2006

(51) Int. Cl.
*A61B 6/00* (2006.01)
(52) U.S. Cl. .......................................................... 378/4
(58) Field of Classification Search ................ 378/420, 378/19, 901
See application file for complete search history.

(56) References Cited

U.S. PATENT DOCUMENTS

| | | | | |
|---|---|---|---|---|
| 5,728,691 | A * | 3/1998 | Corpi Constantino | 514/202 |
| 6,108,575 | A * | 8/2000 | Besson | 600/425 |
| 6,263,040 | B1 | 7/2001 | Hsieh | |
| 6,266,388 | B1 | 7/2001 | Hsieh | |
| 6,421,411 | B1 * | 7/2002 | Hsieh | 378/4 |
| 6,421,552 | B1 * | 7/2002 | Hsieh | 600/425 |
| 6,678,346 | B2 * | 1/2004 | Hsieh | 378/4 |
| 6,754,299 | B2 * | 6/2004 | Patch | 378/15 |
| 6,865,246 | B2 * | 3/2005 | Yang | 378/4 |
| 6,999,550 | B2 * | 2/2006 | Tang | 378/15 |
| 2002/0113215 | A1 * | 8/2002 | Danielsson et al. | 250/492.1 |
| 2002/0122528 | A1 * | 9/2002 | Besson | 378/4 |
| 2003/0007604 | A1 * | 1/2003 | Hsieh et al. | 378/210 |
| 2003/0123614 | A1 * | 7/2003 | Silver et al. | 378/146 |
| 2004/0252806 | A1 * | 12/2004 | Taguchi et al. | 378/4 |
| 2005/0175144 | A1 * | 8/2005 | Hsieh | 378/19 |

OTHER PUBLICATIONS

Grass et al., 3D cone-beam CT reconstruction for circular trajectories, Phys. Med Biol, 2000, pp. 329-347.*
Rodet et al., The cone-beam algorithm of Feldkamp, Davis, and Kress preserves oblique line integrals, Med Physic, vol. 31, Mar. 2004, pp. 1-9.*
Kudo et al., Derivation and Implementation of a Cone-beam Reconstruction Algorithm for Nonplanr Orbits, IEEE Transactions on Medical Imaging, vol. 13, No. 1, Mar. 1994, pp. 196-211.*
Yan et al., Cone beam tomography with circular, elliptical and spiral orbits, Phys. Med. Biol., 1992, vol. 37, No. 3, pp. 493-506.*
Feldkamp et al., Practical Cone-beam Algorithm, Optical Society of America, vol. 1, No. 6, Jun. 1984, pp. 612-619.*
Thomas Rodet et al.; "The cone-beam algorithm of Feldkamp, Davis and Kress preserves oblique line integrals"; Dept. of Nuclear Medicine, Vrije Universiteit Brusel, AZ-VUB, B-1090 Brussels, Belgium and Dept. of Radiology, University of Utah, Salt-Lake City, Utah, Mar. 9, 2004, pp. 1-9.

(Continued)

*Primary Examiner*—Edward J Glick
*Assistant Examiner*—Alexander H Taningco
(74) *Attorney, Agent, or Firm*—Armstrong Teasdale LLP

(57) ABSTRACT

Methods and systems for generating images from a set of projection data acquired during a CT scan is provided. The system includes a computer programmed to utilize at least one of a cone angle dependent view weighting and an image plane dependent view weighting to generate an image.

25 Claims, 4 Drawing Sheets

OTHER PUBLICATIONS

Hiroyuki Kudo et al.: "Exact and approximate algorithms for helical cone-beam CT": Dept. of Computer Science, Graduate School of Systems and Information Engineering, University of Tsukua, Japan; Dept. of Nuclear Medicine, Vrije Uniiversiteit Brusses, AZ-VUB, B 1090 Brussels, Belgium; Dept of Radiology, University of Utah, Salt-Lake City, Utah, Apr. 27, 2004, pp. 1-26.

Xiangyang-Tang et al.; "An Efficient Cone Beam Filtered Backprojection (CB-FBP) Reconstruction Algorithm for a Circle-plus-two-arc Orbit"; Department of Radiology, Department of Electrical and Computer Engineering, University of Rochester, Rochester, NY, USA, IEEE, 2001, pp. 15-126 through 15-130.

Sun Yi, et al.; "Radiography, An Improved Cone-Beam Filtered Backprojection Reconstruction Algorithm Based on X-Ray Angular Correction and Multiresolution Analysis" 16TH WCNDT 2004—World Conference on NDT, Aug. 30-Sep. 3, 2004, Montreal, Canada; Session Abstract, NDT.net, 1 page.

Sun Yi, et al.; "Radiography, An Improved Cone-Beam Filtered Backprojection Reconstruction Algorithm Based on X-Ray Angular Correction and Multiresolution Analysis" 16TH WCNDT 2004—World Conference on NDT, Aug. 30-Sep. 3, 2004, Montreal, Canada; School of Electronic and Information Engineering, Dalian University of Technology, P.R.China, 5 pages.

L.A. Feldkamp et al.; "Practical cone-beam algorithm" Journal of Optical Society of America, vol. 1, No. 6, Jun. 1984; pp. 612-619.

* cited by examiner

METHODS AND SYSTEMS TO FACILITATE REDUCING CONE BEAM ARTIFACTS IN IMAGES

BACKGROUND OF THE INVENTION

This invention relates generally to computed tomography (CT) imaging and more particularly, to reducing cone beam artifacts in CT images.

The original Feldkamp, Davis, and Kress (FDK) algorithm for a circular trajectory has been extensively employed in medical and industrial imaging applications. With increasing cone angle, cone beam (CB) artifacts associated with the FDK algorithm deteriorate, because a circular trajectory does not satisfy the so-called data sufficiency condition (DSC). A few "circular plus" trajectories, such as "circle+circle", "ellipse+ellipse", "circle+line", "circle+arc", have been proposed to facilitate reducing CB artifacts by meeting the DSC. However, the circular trajectory possesses advantages in medical imaging, such as perfusion, cardiac and vascular imaging, as well as breast and head imaging applications.

BRIEF DESCRIPTION OF THE INVENTION

In one embodiment, a computer programmed to generate computed tomographic (CT) images from a set of projection data acquired during a CT scan is provided. The computer is programmed to perform at least one of a cone angle dependent view weighting and an image plane dependent view weighting.

In another embodiment, a method for producing a cross-sectional image of an object by using a computed tomography imaging system is provided. The system includes a source of a conical beam of radiation and a multi-row detector array arranged on opposite sides of an axis of rotation. The method includes rotating the source and detector array about the axis of rotation, and while rotating, collecting x-ray attenuation data samples from the multi-row detector array at a plurality of projection angles to produce a set of projection data measured with a circular orbit of the x-ray source. The method further includes applying a filtered-backprojection algorithm to the set of projection data. The algorithm includes at least one of a cone angle dependent view weighting and an image plane dependent view weighting.

In yet another embodiment, a computed tomographic (CT) imaging system for reconstructing an image of an object is provided. The imaging system includes a detector array, at least one radiation source, and a computer coupled to the detector array and the radiation source. The computer is configured to apply a cone-angle-and-image-plane-dependent view weighting function to a filtered backprojection algorithm to reconstruct three dimensional images from cone-beam projections measured with a circular orbit of the radiation source, and generate images using the view weighted filtered backprojection algorithm.

DETAILED DESCRIPTION OF THE INVENTION

Figure 1:
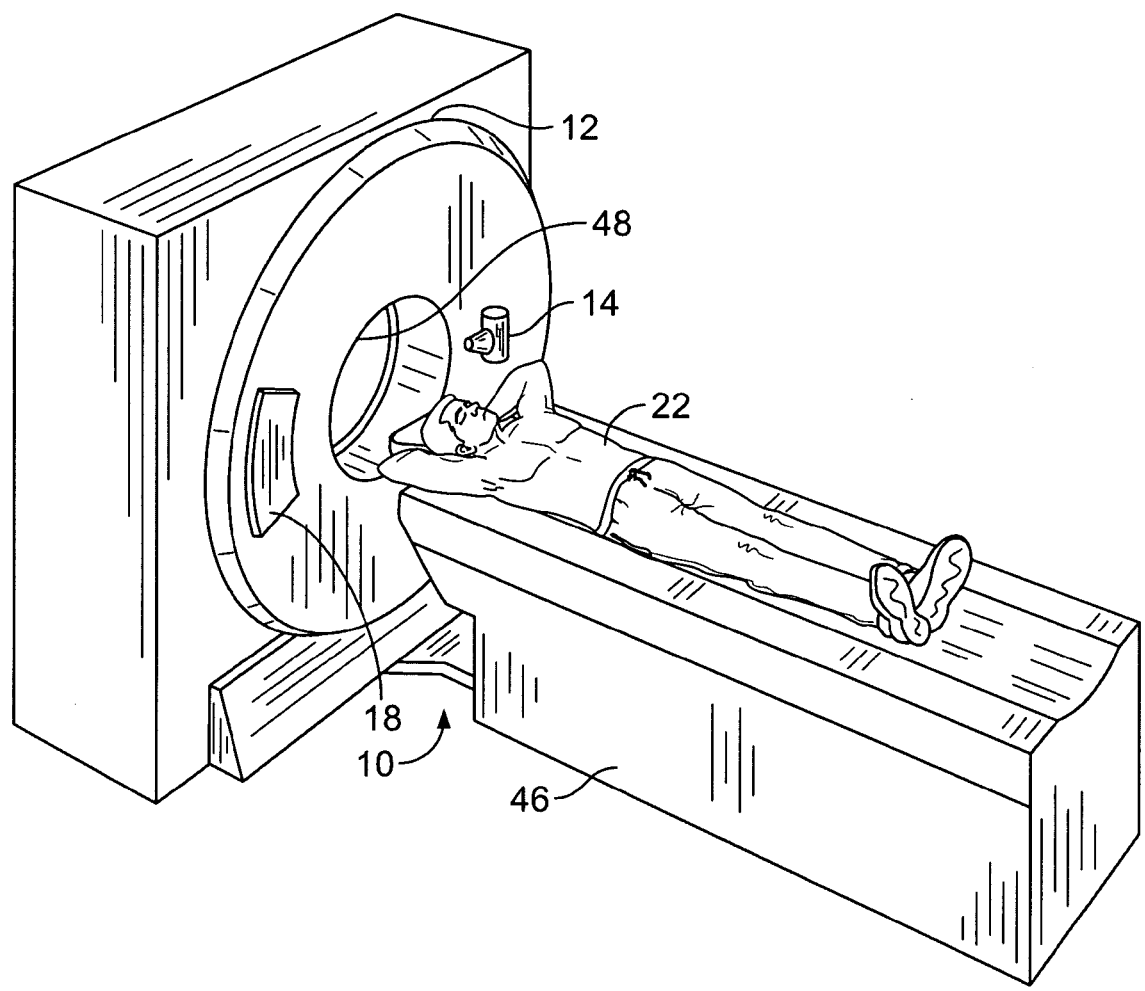
FIG. 1 is a pictorial view of a multi slice volumetric CT imaging system.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image. Additionally, although described in detail in a CT medical setting, it is contemplated that the benefits accrue to all imaging modalities including, for example, ultrasound, Magnetic Resonance Imaging, (MRI), Electron Beam CT (EBCT), Positron Emission Tomography (PET), Single Photon Emission Computed Tomography (SPECT), and in both medical settings and non-medical settings such as an industrial setting or a transportation setting, such as, for example, but not limited to, a baggage scanning CT system for an airport or other transportation center.

Figure 2:
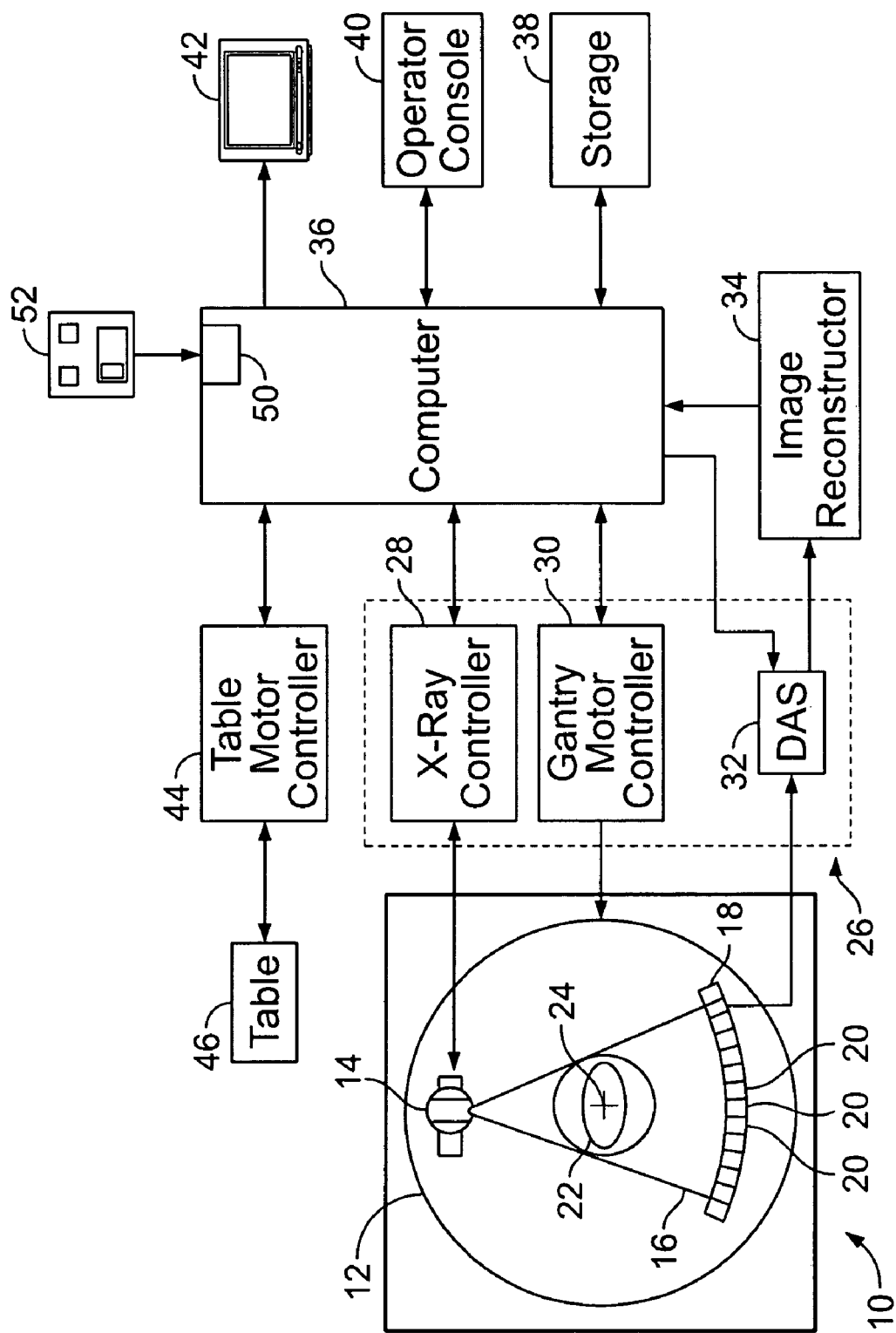
FIG. 2 is a block schematic diagram of the multi slice volumetric CT imaging system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 3:
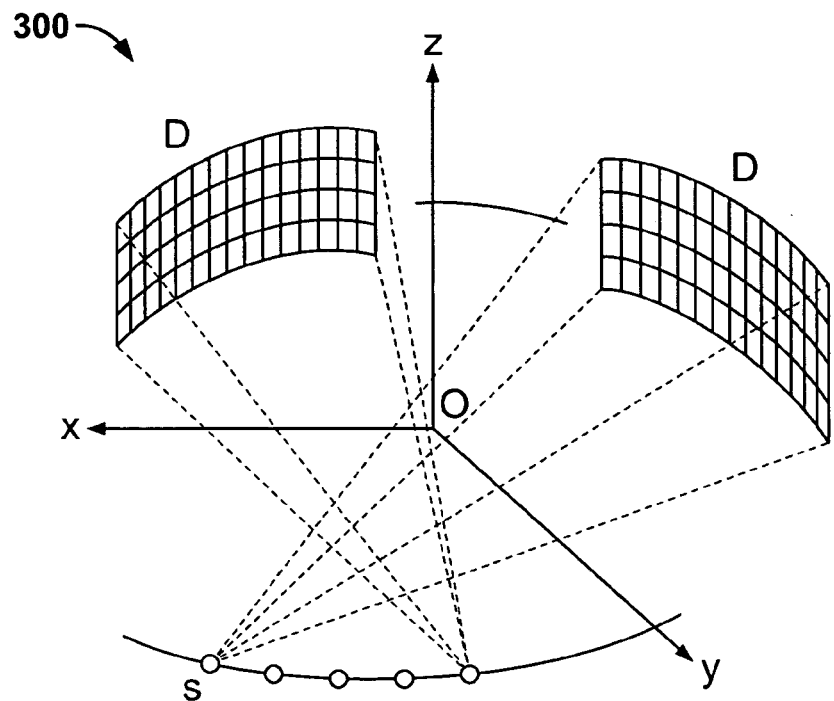
FIG. 3 is a schematic illustration of an exemplary cone beam (CB) geometry that may be used with the imaging system shown in FIG. 1.
Figure 4:
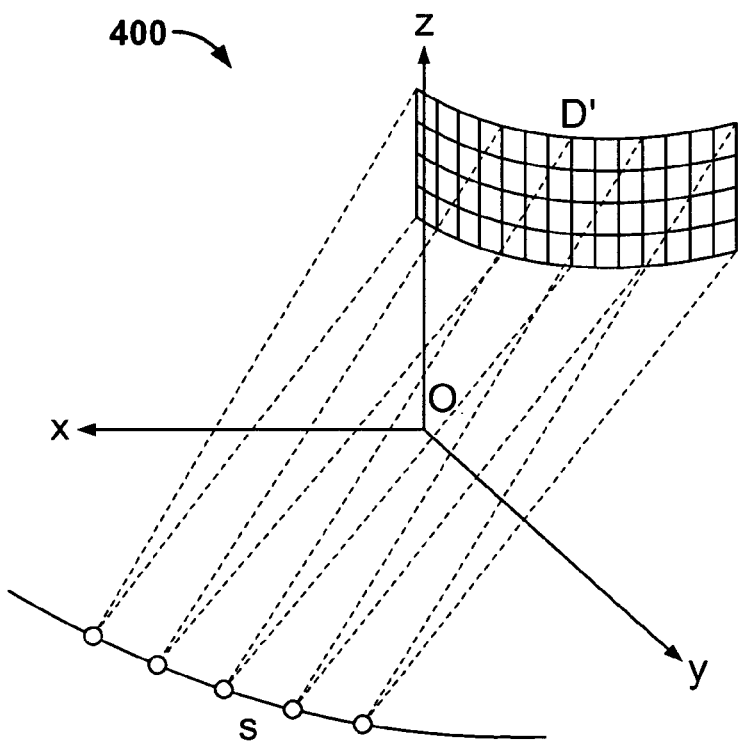
FIG. 4 is a schematic illustration of an exemplary cone-parallel geometry, which can be obtained by a row-wise fan-to-parallel rebinning in the original CB geometry shown in FIG. 3.

FIG. 3 is a schematic illustration of an exemplary cone beam (CB) geometry 300 that may be used with system 10 (shown in FIG. 1). FIG. 4 is a schematic illustration of an exemplary cone-parallel geometry 400, which can be obtained by a row-wise fan-to-parallel rebinning in the original CB geometry (shown in FIG. 3). In the exemplary embodiment, a CB reconstruction algorithm using cone-angle-and-image-plane-dependent view weighting is described using the cone-parallel geometry.

The Feldkamp, Davis, and Kress (FDK) algorithm based on the cone-parallel geometry can be expressed as:

$$f(x, y, z) = \frac{1}{2}\int_0^{2\pi}\left[d^2/(d^2+Z^2)^{1/2}\right]\left[\int_{-\infty}^{+\infty}S_\beta(\omega, Z)e^{j2\pi\omega x}|\omega|d\omega\right]d\beta, \quad (1)$$

and $$S_\beta(\omega, Z) = \int_{-\infty}^{\infty}P_\beta(t, Z)e^{-j2\pi\omega t}dt, \quad (2)$$

where, β represents the view angle;

$f(x,y,z)$ represents the point to be reconstructed;

$P_\beta(t,Z)$ represents the projection of $f(x,y,z)$ in the virtual detector D';

d represents the orthogonal distance between the x-ray focal spot and the virtual detector; and Z represents the height of the projection of $f(x,y,z)$ in the virtual detector.

In addition to the recognition that the generation of CB artifacts in images reconstructed by the FDK algorithm is because the FDK algorithm does not satisfy the DSC, another insight into the root cause of the CB artifacts is that there exist inconsistence between conjugate rays. Conjugate rays are rays that are 180° apart in view angle.

Figure 5:
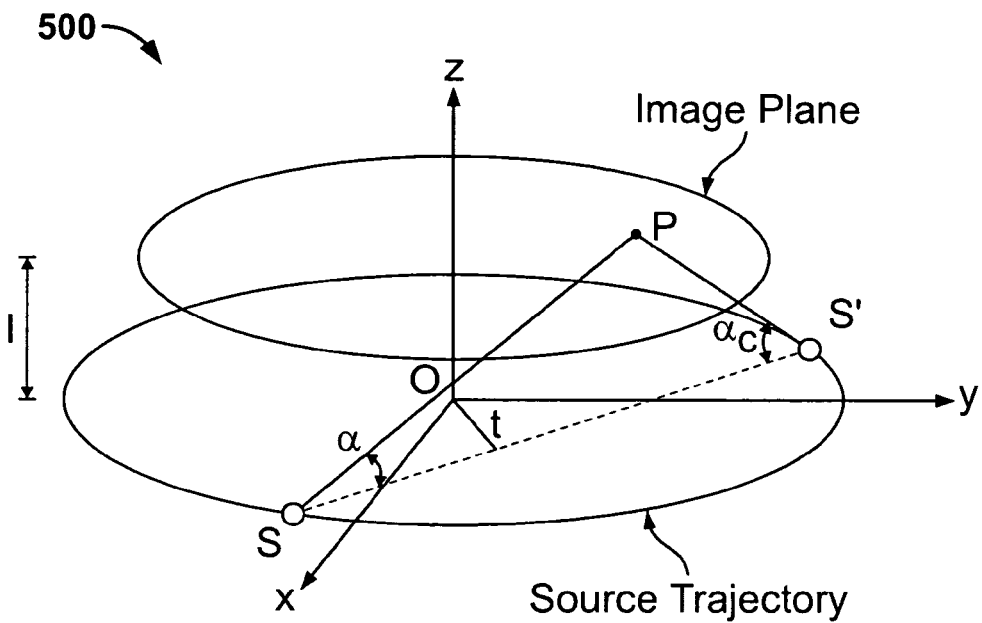
FIG. 5 is a schematic diagram of an exemplary geometry of a direct-ray and its conjugate ray.

FIG. 5 is a schematic illustration of an exemplary geometry 500 of a direct-ray and its conjugate ray. In the exemplary embodiment, ray SP is the direct ray determined by (α,β,t), S'P is the conjugate ray determined by (α_c,β+π,−t), t is the orthogonal distance between O and line SS', and l the distance between the image plane and the central plane determined by the circular source trajectory.

Direct ray SP and its conjugate ray S'P do not pass through the same path. This difference is called "inconsistence" and is pixel dependent. The inconsistence varies dramatically over the location of pixels to be reconstructed. Moreover, the larger the distance between an image plane (IP) in which the image is to be reconstructed and the central plane (CP) determined by the circular trajectory, the more severe the inconsistency over image pixels. As shown in equations (1)-(2), the FDK algorithm treats all rays equally, resulting in CB artifacts that can be reduced if an appropriate view weighting strategy is exercised.

Without extra trajectories supplemental to the circular trajectory, the modified FDK algorithm described herein applies a cone-angle-dependent view weighting on projection data. The cone-angle-dependent view weighting significantly reduces the inconsistency between conjugate rays by suppressing the contribution from one of the conjugate samples with a larger cone angle. Furthermore, the view weighting's dependence on cone-angle should increase with the distance between IP and CP, because the inconsistency severity of the pixels within an IP is proportional to the distance. Inclusively, based on the cone-parallel geometry illustrated in FIG. 4, the modified FDK algorithm can be expressed as $$f(x, y, z) = \frac{1}{2}\int_0^{2\pi}[d^2/(d^2+Z^2)^{1/2}]\left[\int_{-\infty}^{+\infty}w(l,\alpha)S_\beta(\omega,Z)e^{j2\pi\omega x}|\omega|d\omega\right]d\beta, \quad (3)$$

and $$S_\beta(\omega, Z) = \int_{-\infty}^{\infty}P_\beta(t, Z)e^{-j2\pi\omega t}dt. \quad (4)$$

where $\alpha$ represents the cone angle of the ray emanating from the focal spot and passing through point P;

l is the orthogonal distance between IP and CP; and $w(l, \alpha)$ is the cone-angle-and-image-plane-dependent view weighting function.

Generally, the view weighting function $w(l,\alpha)$ meets the following conditions:

$$0 \leq w(l,\alpha) \leq 1.0 \quad (5)$$

$$w(l,\alpha_1) \geq w(l,\alpha_2) \text{ while } \alpha_1 \leq \alpha_2, \quad (6)$$

and a special case of the view weighting function $w(l,\alpha)$ is given below as an example:

$$w(l, \alpha) = \frac{\tan^{g(l)}\alpha_c}{\tan^{g(l)}\alpha + \tan^{g(l)}\alpha_c} \quad (7)$$

where g(l) is a positive monotonically increasing function over the distance l, for example, $$g(l) \geq 0 \quad (8)$$

$$g(l_1) \leq g(l_2) \text{ while } l_1 \leq l_2 \quad (9)$$

A mechanism underlying the modified FDK algorithm described in equations (3)-(9) is that one of the conjugate rays with smaller cone angle is given a favorable weight while the other with larger cone angle is given a smaller weight.

Generally, if IP is far away from the CP or close to the boundary row of a detector, data extrapolation is needed for 3D backprojection to reconstruct the image. Given a pixel P to be reconstructed, it is possible for one of the conjugate rays passing through pixel P to hit inside of the detector, but the other ray to hit outside of the detector. The conjugate rays hitting inside of the detector should be given larger weight, while the rays hitting outside of the detector should earn a smaller weight. This can be done by incorporating an extra term in equations (7)~(9) as shown below:

$$w(l, \alpha, z) = \frac{\tan^{(g(l)+f(v_c))}\alpha_c}{\tan^{(g(l)+f(v))}\alpha + \tan^{(g(l)+f(v_c))}\alpha_c} \quad (10)$$

where v and $v_c$ are the vertical coordinates of the projection of pixel P in the detector corresponding to each of the conjugate rays, respectively. $f(v)$ and $f(v_c)$ can be defined as:

$$f(v) = \begin{cases} f'(v) > 0 & \text{while } |v| > D \\ 0 & \text{while } |v| \leq D \end{cases} \quad (11)$$

$$f(v_c) = \begin{cases} f'(v_c) > 0 & \text{while } |v_c| > D \\ 0 & \text{while } |v_c| \leq D \end{cases} \quad (12)$$

where D is the half height of the detector.

Both $f'(v)$ and $f'(v_c)$ are positive monotonous increasing functions, i.e., $$f'(v_1) \leq f'(v_2) \text{ while } v_1 \leq v_2 \quad (13)$$

$$f'(v_{c1}) \leq f'(v_{c2}) \text{ while } v_{c1} \leq v_{c2} \quad (14)$$

The mechanism underlying equations (10)-(14) is that, one of the conjugate rays inside the active area of the detector is given an enhanced favorable weight while the other with larger cone angle is given an enhanced unfavorable weight.

Moreover, the cone-angle-and-image-plane-dependent view weighting can be extended to implement the so-called "cross-beam correction", in which more than one circular source trajectories apart in z-direction are utilized to improve the image quality of the images between the CPs determined by those circular trajectories.

Figure 6:
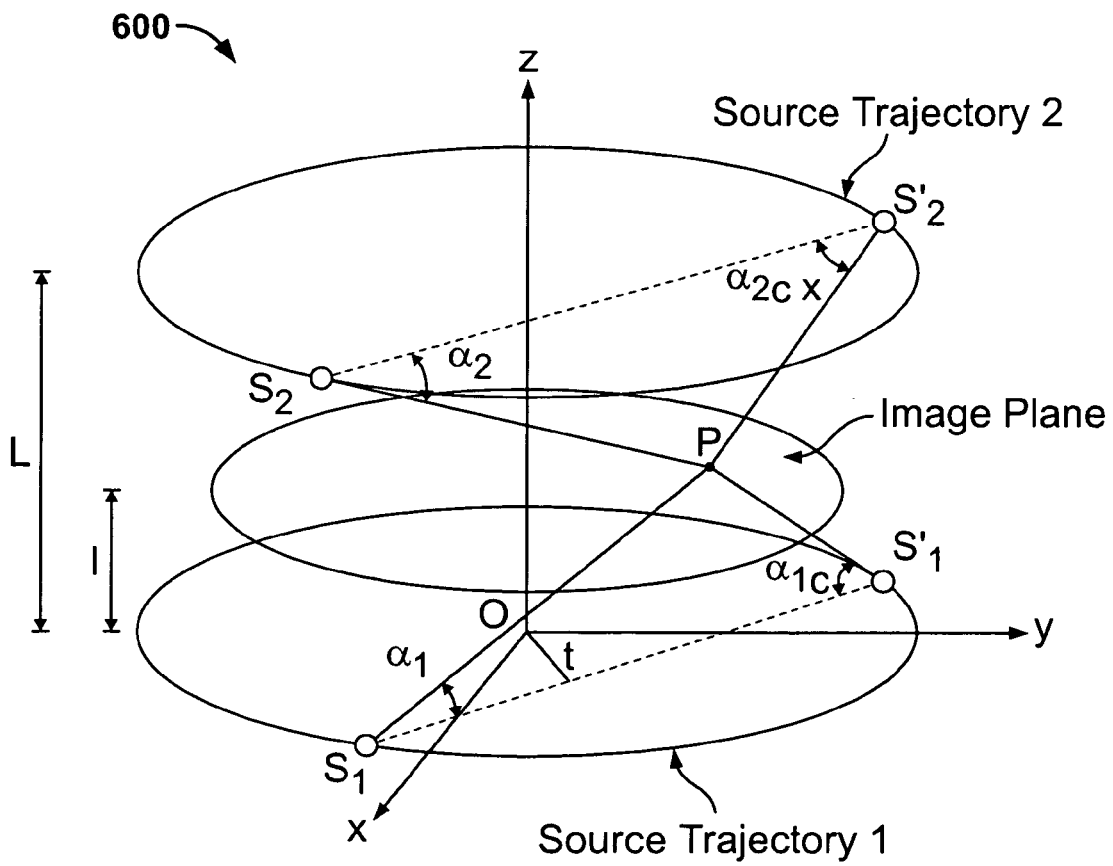
FIG. 6 is a schematic diagram of an exemplary geometry of direct-rays and conjugate rays associated with a dual circular trajectory.

FIG. 6 is a schematic illustration of an exemplary geometry 600 of direct-rays and conjugate rays associated with a dual circular trajectories. Ray $S_1P$ ($\alpha_1,\beta,t$) and $S'_1P$ ($\alpha_{1c}, \beta+\pi,-t$) are the conjugate rays corresponding to trajectory 1, and ray $S_2P$ ($\alpha_2,\beta,t$) and $S'_2P$ ($\alpha_{2c},\beta+\pi,-t$) are the conjugate rays corresponding to trajectory 2. The distance between the IP and trajectory 1 is l, and the distance between the IP and trajectory 2 is L-l. For each trajectory, the view weighting function is defined as:

$$w_1(l, \alpha, z) = 0.5\frac{\tan^{g(l)}\alpha_{1c}}{\tan^{g(l)}\alpha_1 + \tan^{g(l)}\alpha_{1c}}, \quad (15)$$

$$w_2(l, \alpha, z) = 0.5\frac{\tan^{g(L-l)}\alpha_{2c}}{\tan^{g(L-l)}\alpha_2 + \tan^{g(L-l)}\alpha_{2c}}. \quad (16)$$

The above-described embodiments of an imaging system facilitate reducing cone beam artifacts. Exemplary embodiments of imaging system methods and apparatus are described above in detail. The imaging system components illustrated are not limited to the specific embodiments described herein, but rather, components of each imaging system may be utilized independently and separately from other components described herein. For example, the imaging system components described above may also be used in combination with different imaging systems. A technical effect of the various embodiments of the systems and methods described herein include at least one of facilitating imaging a patient with images wherein the cone beam artifacts have been substantially reduced.

While the invention has been described in terms of various specific embodiments, those skilled in the art will recognize that the invention can be practiced with modification within the spirit and scope of the claims.

What is claimed is:

1. A computer programmed to generate computed tomographic (CT) images from a set of projection data acquired during a CT scan, said computer programmed to:

perform a cone-angle-and-image-plane-dependent view weighting, wherein the view weighting is at least partially defined by an orthogonal distance between an image plane and a central plane;

apply a Feldkamp, Davis, and Kress (FDK) algorithm with the cone-angle-and-image-plane-dependent view weighting to the set of projection data;

apply an FDK algorithm to a single circular source trajectory expressed as:

$$f(x, y, z) = \frac{1}{2}\int_0^{2\pi}\left[d^2/(d^2+Z^2)^{1/2}\right]\left[\int_{-\infty}^{+\infty}w(l,\alpha)S_\beta(\omega,Z)e^{j2\pi\omega x}|\omega|d\omega\right]d\beta;$$

and $$S_\beta(\omega, Z) = \int_{-\infty}^{\infty}P_\beta(t, Z)e^{-j2\pi\omega t}dt,$$

where w(X) represents at least one of:

$$w(l, \alpha) = \frac{\tan^{g(l)}\alpha_c}{\tan^{g(l)}\alpha + \tan^{g(l)}\alpha_c}$$

$$w(l, \alpha, z) = \frac{\tan^{(g(l)+f(v_c))}\alpha_c}{\tan^{(g(l)+f(v))}\alpha + \tan^{(g(l)+f(v_c))}\alpha_c},$$

where
β represents view angle;
$f(x,y,z)$ represents the point to be reconstructed;
$P_\beta(t,Z)$ represents the projection of $f(x,y,z)$ in the virtual detector D';
d represents the orthogonal distance between the x-ray focal spot and the virtual detector;
Z represents the height of the projection of $f(x,y,z)$ in the virtual detector;
ω represents frequency;
$\alpha\equiv\alpha(x,y,z)$ that represents the cone angle of the ray emanating from the focal spot and passing through a point P, wherein $\alpha(x,y,z)$ is dependent on a coordinate (x,y,z) of the point P;
$l\equiv l(z)$ that represents an orthogonal distance between an imaging plane (IP) and a central plane (CP), wherein l(z) is dependent on a z-coordinate of the point P g(l) is a positive monotonically increasing function over distance l;
$\alpha_c$ represents a cone angle of a conjugate ray to the ray emanating from the focal spot and passing through a point P; and
v and $v_c$ are the vertical coordinates of the projection of pixel P in the detector corresponding to each conjugate ray, respectively.

2. A computer in accordance with claim 1 wherein the cone-angle-and-image-plane-dependent view weighting function w(l,α) meets conditions:

$0 \leq w(l,\alpha) \leq 1.0$ and $w(l,\alpha_1) \geq w(l,\alpha_2)$ while $|\alpha_1| \leq |\alpha_2|$.

3. A computer in accordance with claim 1 wherein conjugate rays are rays that are 180° apart in view angle, said computer further programmed to weight a first ray associated with a relatively larger cone angle less than a second ray associated with a relatively smaller cone angle, the rays being conjugates with respect to each other.

4. A computer in accordance with claim 1 wherein one of a ray passing through a pixel P and a conjugate of the ray impinge on a detector, said computer further programmed to weight the ray impinging the detector relatively greater than the ray not impinging the detector when reconstructing pixel P.

5. A computer in accordance with claim 1 wherein g(l) meets the following conditions:

$g(l) \geq 0$, and $g(l_1) \leq g(l_2)$ while $l_1 \leq l_2$.

6. A computer in accordance with claim 1 wherein $f(v)$ and $f(v_c)$ are defined as:

$$f(v) = \begin{cases} f'(v) > 0 & \text{while } |v| > D \\ 0 & \text{while } |v| \leq D \end{cases},$$

and $$f(v_c) = \begin{cases} f'(v_c) > 0 & \text{while } |v_c| > D \\ 0 & \text{while } |v_c| \leq D \end{cases}.$$

7. A computer in accordance with claim 6 wherein $f'(v)$ and $f'(v_c)$ are positive monotonous increasing functions of |v| and $|v_c|$.

8. A computer in accordance with claim 6 wherein $f'(v)$ and $f'(v_c)$ meet the conditions:

$f'(v_1) \leq f'(v_2)$ while $|v_1| \leq |v_2|$, and $f'(v_{c1}) \leq f'(v_{c2})$ while $|v_{c1}| \leq |v_{c2}|$.

9. A computer programmed to generate computed tomographic (CT) images from a set of projection data acquired during a CT scan, said computer programmed to:

perform a cone-angle-and-image-plane-dependent view weighting, wherein the view weighting is at least partially defined by an orthogonal distance between an image plane and a central plane;

apply an FDK algorithm to more than one circular source trajectory spaced apart in the z-direction that define respective central planes such that a distance between the image plane and a first trajectory is l, and a distance between the IP and a second trajectory is L−l and wherein the more than one circular source trajectory are expressed as:

$$f_1(x, y, z) =$$
$$\frac{1}{2}\int_0^{2\pi}\left[d^2/(d^2+Z^2)^{1/2}\right]\left[\int_{-\infty}^{+\infty}w_1(l,\alpha,z)S_\beta(\omega,Z)e^{j2\pi\omega x}|\omega|d\omega\right]d\beta;$$

$$f_2(x, y, z) =$$
$$\frac{1}{2}\int_0^{2\pi}\left[d^2/(d^2+Z^2)^{1/2}\right]\left[\int_{-\infty}^{+\infty}w_2(l,\alpha,z)S_\beta(\omega,Z)e^{j2\pi\omega x}|\omega|d\omega\right]d\beta; \text{ and}$$

$$S_\beta(\omega, Z) = \int_{-\infty}^{+\infty} P_\beta(t, Z) e^{-j2\pi\omega t} dt, \text{ where}$$

$$w_1(l, \alpha, z) = 0.5 \frac{\tan^{g(l)}\alpha_{1c}}{\tan^{g(l)}\alpha_1 + \tan^{g(l)}\alpha_{1c}},$$

$$w_2(l, \alpha, z) = 0.5 \frac{\tan^{g(L-l)}\alpha_{2c}}{\tan^{g(L-l)}\alpha_2 + \tan^{g(L-l)}\alpha_{2c}}.$$

where β represents view angle;
ƒ(x,y,z) represents the point to be reconstructed;
$P_\beta(t,Z)$ represents the projection of ƒ(x,y,z) in the virtual detector D';
where $\alpha_{1c}$ represents a cone angle of a first conjugate ray to the ray emanating from the focal spot and passing through a point P;
where $\alpha_{2c}$ represents a cone angle of a second conjugate ray to the ray emanating from the focal spot and passing through a point P;
where g(l) is a positive monotonically increasing function over distance l;
d represents the orthogonal distance between the x-ray focal spot and the virtual detector;
Z represents the height of the projection of l(x,y,z) in the virtual detector;
ω represents frequency;
$\alpha\_=\alpha(x,y,z)$ that represents the cone angle of the ray emanating from the focal spot and passing through a point P, wherein α(x,y,z) is dependent on a coordinate (x,y,z) of the point P; and
l=l(z) that represents an orthogonal distance between an imaging plane (IP) and a central plane (CP), wherein l(z) is dependent on a z-coordinate of the point P.

10. A method for producing a cross-sectional image of an object by using a computed tomography imaging system, which includes a source of a conical beam of radiation and a multi-row detector array arranged on opposite sides of an axis of rotation, said method comprising:

rotating the source and detector array about the axis of rotation;
while rotating, collecting x-ray attenuation data samples from the multi-row detector array at a plurality of projection angles to produce a set of projection data measured with a circular orbit of the x-ray source; and
generating an image using a Feldkamp, Davis, and Kress (FDK) algorithm from the set of projection data using a cone-angle-and-image-plane-dependent view weighting, wherein the view weighting is at least partially defined by an orthogonal distance between an image plane and a central plane, wherein the FDK algorithm is applied to a single circular source trajectory expressed as:

$$f(x, y, z) =$$
$$\frac{1}{2}\int_0^{2\pi}\left[d^2/(d^2+Z^2)^{1/2}\right]\left[\int_{-\infty}^{+\infty}w(l,\alpha)S_\beta(\omega,Z)e^{j2\pi\omega x}|\omega|d\omega\right]d\beta;$$
and $$S_\beta(\omega, Z) = \int_{-\infty}^{\infty} P_\beta(t, Z) e^{-j2\pi\omega t} dt$$

where w(X) represents at least one of:

$$w(l, \alpha) = \frac{\tan^{g(l)}\alpha_c}{\tan^{g(l)}\alpha + \tan^{g(l)}\alpha_c}$$

$$w(l, \alpha, z) = \frac{\tan^{(g(l)+f(v_c))}\alpha_c}{\tan^{(g(l)+f(v))}\alpha + \tan^{(g(l)+f(v_c))}\alpha_c},$$

$$w_1(l, \alpha, z) = 0.5 \frac{\tan^{g(l)}\alpha_{1c}}{\tan^{g(l)}\alpha_1 + \tan^{g(l)}\alpha_{1c}},$$

$$w_2(l, \alpha, z) = 0.5 \frac{\tan^{g(L-l)}\alpha_{2c}}{\tan^{g(L-l)}\alpha_2 + \tan^{g(L-l)}\alpha_{2c}}.$$

β represents view angle;
ƒ(x,y,z) represents the point to be reconstructed;
$P_\beta(t,Z)$ represents the projection of ƒ(x,y,z) in the virtual detector D';
d represents the orthogonal distance between the x-ray focal spot and the virtual detector;
Z represents the height of the projection of ƒ(x,y,z) in the virtual detector;
ω represents frequency;
w(l,α) represents a cone-angle-and-image-plane-dependent view weighting function;
$\alpha\_=\alpha(x,y,z)$ that represents the cone angle of the ray emanating from the focal spot and passing through a point P, wherein α(x,y,z) is dependent on a coordinate (x,y,z) of the point P;
l=l(z) that represents an orthogonal distance between an imaging plane (IP) and a central plane (CP), wherein l(z) is dependent on a z-coordinate of the point P
g(l) is a positive monotonically increasing function over distance l;
$\alpha_c$ represents a cone angle of a conjugate ray to the ray emanating from the focal spot and passing through a point P
v and $v_c$ are the vertical coordinates of the projection of pixel P in the detector corresponding to each conjugate ray, respectively;
where $\alpha_{1c}$ represents a cone angle of a first conjugate ray to the ray emanating from the focal spot and passing through a point P; and
where $\alpha_{2c}$ represents a cone angle of a second conjugate ray to the ray emanating from the focal spot and passing through a point P.

11. A method in accordance claim 10 wherein cone-angle-and-image-plane-dependent view weighting function w(l,α) meets conditions:

$0 \le w(l,\alpha) \le 1.0$ and $w(l,\alpha_1) \ge w(l,\alpha_2)$ while $|\alpha_1| \le |\alpha_2|$.

12. A method in accordance with claim 10 wherein conjugate rays are rays that are 180° apart in view angle, said method further comprising weighting a first ray associated with a relatively larger cone angle less than a second ray associated with a relatively smaller cone angle, the rays being conjugates with respect to each other.

13. A method in accordance with claim 10 wherein one of a ray passing through a pixel P and a conjugate of the ray impinge on the detector, said method further comprising weighting the ray impinging the detector relatively greater than the ray not impinging the detector when reconstructing pixel P.

14. A method in accordance with claim 10 wherein g(l) meets the following conditions:

$g(l) \ge 0$, and $g(l_1) \le g(l_2)$ while $l_1 \le l_2$.

15. A method in accordance with claim 10 wherein $f(v)$ and $f(v_c)$ are defined as:

$$f(v) = \begin{cases} f'(v) > 0 & \text{while } |v| > D \\ 0 & \text{while } |v| \le D \end{cases}, \text{ and}$$

$$f(v_c) = \begin{cases} f'(v_c) > 0 & \text{while } |v_c| > D \\ 0 & \text{while } |v_c| \le D \end{cases}.$$

16. A method in accordance with claim 15 wherein $f'(v)$ and $f'(v_c)$ are positive monotonous increasing functions.

17. A method in accordance with claim 16 wherein $f'(v)$ and $f'(v_c)$ meet the conditions:

$f'(v_1) \le f'(v_2)$ while $|v_1| \le |v_2|$, and $f'(v_{c1}) \le f'(v_{c2})$ while $|v_{c1}| \le |v_{c2}|$.

18. A computed tomographic (CT) imaging system for reconstructing an image of an object, said imaging system comprising:
a detector array;
at least one radiation source; and
a computer coupled to said detector array and said radiation source, said computer configured to utilize a cone-angle-and-image-plane-dependent view weighting function to generate three-dimensional images from cone-beam projections measured with a circular orbit of the radiation source, wherein the view weighting is at least partially defined by an orthogonal distance between an image plane and a central plane wherein said cone-angle-and-image-plane-dependent view weighting function to the FDK algorithm is expressed as:

$$f(x,y,z) = \frac{1}{2}\int_0^{2\pi}\left[d^2/(d^2+Z^2)^{1/2}\right]\left[\int_{-\infty}^{+\infty}w(l,\alpha)S_\beta(\omega,Z)e^{j2\pi\omega x}|\omega|d\omega\right]d\beta;$$

and $$S_\beta(\omega,Z) = \int_{-\infty}^{\infty}P_\beta(t,Z)e^{-j2\pi\omega t}dt$$

where w(X) represents at least one of:

$$w(l,\alpha) = \frac{\tan^{g(l)}\alpha_c}{\tan^{g(l)}\alpha + \tan^{g(l)}\alpha_c}$$

$$w(l,\alpha,z) = \frac{\tan^{(g(l)+f(v_c))}\alpha_c}{\tan^{(g(l)+f(v))}\alpha + \tan^{(g(l)+f(v_c))}\alpha_c},$$

$$w_1(l,\alpha,z) = 0.5\frac{\tan^{g(l)}\alpha_{1c}}{\tan^{g(l)}\alpha_1 + \tan^{g(l)}\alpha_{1c}},$$

$$w_2(l,\alpha,z) = 0.5\frac{\tan^{g(L-l)}\alpha_{2c}}{\tan^{g(L-l)}\alpha_2 + \tan^{g(L-l)}\alpha_{2c}}.$$

g(l) is a positive function over distance l;

$\alpha_c$ represents a cone angle of a conjugate ray to the ray emanating from the focal spot and passing through a point P;

v and $v_c$ are the vertical coordinates of the projection of pixel P in the detector corresponding to each conjugate ray, respectively;

$\alpha_{1c}$ represents a cone angle of a first conjugate ray to the ray emanating from the focal spot and passing through a point P;

$\alpha_{2c}$ represents a cone angle of a second conjugate ray to the ray emanating from the focal spot and passing through a point P;

β represents view angle;

$f(x,y,z)$ represents the point to be reconstructed;

$P_\beta(t,Z)$ represents the projection of $f(x,y,z)$ in the virtual detector D';

d represents the orthogonal distance between the x-ray focal snot and the virtual detector;

Z represents the height of the projection of $f(x,y,z)$ in the virtual detector;

ω represents frequency;

$\alpha_\_ \equiv \alpha(x,y,z)$ that represents the cone angle of the ray emanating from the focal spot and passing through a point P, wherein α(x,y,z) is dependent on a coordinate (x,y,z) of the point P; and l≡l(z) that represents an orthogonal distance between an imaging plane (IP) and a central plane (CP) wherein l(z) is dependent on a z-coordinate of the point P.

19. A computer in accordance with claim 18 wherein cone-angle-and-image-plane-dependent view weighting function w(l,α) meets conditions;

$0 \le w(l\alpha) \le 1.0$ and $w(l,\alpha_1) \ge w(l,\alpha_2)$ while $|\alpha_1| \le |\alpha_2|$.

20. An imaging system in accordance with claim 18 wherein conjugate rays are rays that are 180° apart in view angle, said computer further configured to weight a first ray associated with a relatively larger cone angle less than a second ray associated with a relatively smaller cone angle, the rays being conjugates with respect to each other.

21. An imaging system in accordance with claim 18 wherein one of a ray passing through a pixel P and a conjugate of the ray impinge on the detector, said computer further configured to weight the ray impinging the detector relatively greater than the ray not impinging the detector when reconstructing pixel P.

22. An imaging system in accordance with claim 18 wherein g(l) meets the following conditions:

$g(l) \geq 0$, and $g(l_1) \leq g(l_2)$ while $l_1 \leq l_2$.

23. An imaging system in accordance with claim 18 wherein ƒ(v) and ƒ(v$_c$) are defined as;

$$f(v) = \begin{cases} f'(v) > 0 & \text{while } |v| > D \\ 0 & \text{while } |v| \leq D \end{cases}, \text{ and}$$

$$f(v_c) = \begin{cases} f'(v_c) > 0 & \text{while } |v_c| > D \\ 0 & \text{while } |v_c| \leq D \end{cases}.$$

24. An imaging system in accordance with claim 23 wherein ƒ'(v) and ƒ'(v$_c$) are positive monotonous increasing functions.

25. An imaging system in accordance with claim 24 wherein ƒ'(v) and ƒ'(v$_c$) meet the conditions:

ƒ'(v$_1$)≦ƒ'(v$_2$) while |v$_1$|≦|v$_2$|, and

ƒ'(v$_{c1}$)≦ƒ'(v$_{c2}$) while |v$_{c1}$|≦|v$_{c2}$|.

\* \* \* \* \*

UNITED STATES PATENT AND TRADEMARK OFFICE
CERTIFICATE OF CORRECTION

| | | |
|---|---|---|
| PATENT NO. | : 7,573,973 B2 | Page 1 of 1 |
| APPLICATION NO. | : 11/130769 | |
| DATED | : August 11, 2009 | |
| INVENTOR(S) | : Tang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 671 days.

Signed and Sealed this

Seventh Day of September, 2010

David J. Kappos
*Director of the United States Patent and Trademark Office*